United States Patent [19]

Bell et al.

[11] Patent Number: 5,541,203
[45] Date of Patent: Jul. 30, 1996

[54] TRIAZOLE ANTIFUNGAL AGENTS

[75] Inventors: Andrew S. Bell, Deal; Kenneth Richardson, Birchington; Peter J. Whittle, Canterbury, all of United Kingdom

[73] Assignee: Pfizer Inc., New York, N.Y.

[21] Appl. No.: 211,609

[22] PCT Filed: Oct. 1, 1992

[86] PCT No.: PCT/EP92/02278

§ 371 Date: Apr. 8, 1994

§ 102(e) Date: Apr. 8, 1994

[87] PCT Pub. No.: WO93/07139

PCT Pub. Date: Apr. 15, 1993

[30] Foreign Application Priority Data

Oct. 10, 1991 [GB]  United Kingdom ................ 9121456

[51] Int. Cl.⁶ .................. C07D 401/02; A61K 31/44
[52] U.S. Cl. ............... 514/340; 514/256; 546/272.4; 546/281.7; 546/298; 546/316; 544/333
[58] Field of Search ............. 546/276; 514/340, 514/256; 544/333

[56] References Cited

FOREIGN PATENT DOCUMENTS

| | | | |
|---|---|---|---|
| 052424 | 5/1982 | European Pat. Off. | C07D 249/08 |
| 321211 | 6/1989 | European Pat. Off. | C07D 249/08 |
| 332387 | 9/1989 | European Pat. Off. | C07D 249/08 |
| 357241 | 3/1990 | European Pat. Off. | C07D 249/08 |
| 440372 | 8/1991 | European Pat. Off. | . |
| 3245504 | 12/1982 | Germany | C07D 233/66 |
| 3732385 | 9/1987 | Germany | C07D 233/60 |
| 3813841 | 12/1988 | Germany | C07D 233/60 |
| 322526 | 6/1989 | Germany | C07D 231/12 |
| 8905581 | 6/1989 | WIPO | C07D 249/12 |

OTHER PUBLICATIONS

CA 89:43764g (1978). F. Maurer et al.

Primary Examiner—Jane Fan
Attorney, Agent, or Firm—Peter C. Richardson; Paul H. Ginsburg; Bryan C. Zielinski

[57] ABSTRACT

The invention provides antifungal compounds of the formula:

and the pharmaceutically acceptable salts thereof, wherein
R is phenyl substituted by up to 3 substituents each independently selected from halo and trifluoromethyl;
$R^1$ is $C_1$–$C_4$ alkyl;
$R^2$ is $R^3$ is —$S(O)_m R^4$;
$R^4$ is $C_1$–$C_4$ alkyl; and
m is 0, 1 or 2, together with pharmaceutical compositions containing, and processes and intermediates for preparing, said compounds.

12 Claims, No Drawings

TRIAZOLE ANTIFUNGAL AGENTS

This is a 371 of PCT/EP 92/02278 filed Oct. 1, 1992 now WO 93/07139.

This invention relates to triazole derivatives which have antifungal activity.

More particularly this invention relates to 2-phenyl-3-(pyridinyl or pyrimidinyl)-1-(1H-1,2,4-triazol- 1-yl)alkan-2-ol derivatives which are useful in the treatment of fungal infections in animals, particularly human beings.

Cryptococcosis is a severe systemic fungal infection caused by *Cryptococcus neoformans* with a primary focus in the lung and characteristic spread to the meninges, especially those in the brain, and sometimes to the kidneys, bone and skin. *Cryptococcal meningitis* is a life-threatening fungal infection in up to 30% of AIDS patients.

The compounds of the present invention are surprisingly active against the clinically important *Cryptococcus spp.* fungi and in addition have surprisingly reduced liver toxicity.

The present invention provides compounds of the formula:

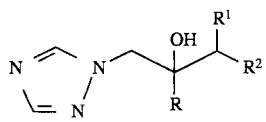

and pharmaceutically acceptable salts thereof, wherein

R is phenyl substituted by up to 3 substituents each independently selected from halo and trifluoromethyl;

$R^1$ is $C_1$–$C_4$ alkyl;

$R^2$ is

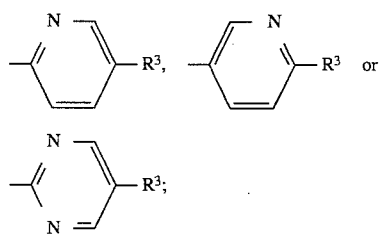

$R^3$ is —$S(O)_m R^4$;

$R^4$ is $C_1$–$C_4$ alkyl; and m is 0, 1 or 2.

The term "halo" means F, Cl, Br or I.

Alkyl groups having three or more carbon atoms may be straight- or branched-chain.

Preferably R is phenyl substituted by 1 or 2 halo substituents.

More preferably R is phenyl substituted by 1 or 2 substituents each independently selected from F and Cl.

Most preferably R is 2,4-difluorophenyl.

Preferably $R^1$ is methyl.

Preferably $R^2$ is

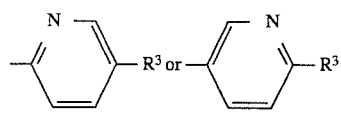

Preferably $R^4$ is methyl.
Preferably m is 2.

The pharmaceutically acceptable salts of the compounds of the formula (I) include acid addition salts formed with acids which form non-toxic salts such as the hydrochloride, hydrobromide, hydroiodide, sulphate, bisulphate, phosphate, hydrogen phosphate, acetate, maleate, fumarate, lactate, tartrate, citrate, gluconate, benzoate, methanesulphonate, benzenesulphonate and para-toluenesulphonate salts. For a review on suitable pharmaceutical salts see Berge et al, J. Pharm. Sci., 66, 1–19 (1977).

The preferred compounds of the formula (I) are 2-(2,4-difluorophenyl)-3-(2-methanesulphonylpyridin-5-yl)-1-(1H-1,2,4-triazol-1-yl)butan-2-ol and 2-(2,4-difluorophenyl)- 3-(5-methanesulphonylpyridin-2-yl)- 1-(1H-1,2,4-triazol-1-yl)butan-2-ol, and the pharmaceutically acceptable salts thereof.

The compounds of the formula (I) contain at least two chiral centres and therefore exist as at least two diastereoisomeric pairs of enantiomers. The invention includes both the individual stereoisomers of the compounds of the formula (I) together with mixtures thereof. Separation of diastereoisomers may be achieved by conventional techniques, e.g. by fractional crystallisation, chromatography or H.P.L.C. of a diastereoisomeric mixture of a compound of the formula (I) or a suitable salt or derivative thereof. An individual enantiomer of a compound of the formula (I) may also be prepared from a corresponding optically pure intermediate or by resolution, either by H.P.L.C. of the racemate using a suitable chiral support or by fractional crystallisation of the diastereoisomeric salts formed by reaction of the racemate with a suitable optically active acid.

The more preferred compounds of the formula (I) are (2R,3S/2S,3R)-2-(2,4-difluorophenyl)-3-(2-methanesulphonylpyridin- 5-yl)-1-(1H-1,2,4-triazol-1-yl)butan- 2-ol and (2R,3S/2S,3R)-2-(2,4-difluorophenyl)-3-( 5-methanesulphonylpyridin-2-yl)-1-(1H-1,2,4-triazol- 1-yl)butan-2-ol and the pharmaceutically acceptable salts thereof.

The compounds of the formula (I) preferably have the (2R,3S)- configuration, i.e.

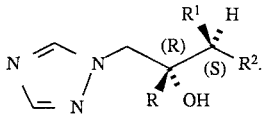

The most preferred compounds of the formula (I) are (2R,3S)-2-(2,4-difluorophenyl)-3-(2-methanesulphonylpyridin- 5-yl)-1-(1H-1,2,4-triazol-1-yl)butan-2-ol and (2R, 3S)-2-(2,4-difluorophenyl)-3-(5-methanesulphonylpyridin-2-yl)-1-(1H-1,2,4-triazol-1-yl)butan-2-ol and the pharmaceutically acceptable salts thereof.

The compounds of the formula (I) provided by the present invention may be prepared by the following methods:

1) The compounds of the formula (I) wherein m is 1 or 2 and R and $R^1$ to $R^4$ are as previously defined for a compound of the formula (I) may be prepared by oxidation of a compound of the formula (I) wherein m is 0 or 1, as appropriate, and R and $R^1$ to $R^4$ are as previously defined for this method.

In a typical procedure the sulphide or sulphoxide, as appropriate, is reacted with a suitable oxidising agent, e.g. a peroxy acid such as meta-chloroperoxybenzoic acid, in a suitable organic solvent, e.g. dichloromethane. The oxidation may be carried out at about room temperature but cooling is often advisable to moderate the reaction. The skilled person will appreciate that when converting a sulphide to a sulphoxide the quantity of oxidising agent used should be limited to about one molar equivalent with respect to the substrate in order to reduce the possibility of sulphone formation. When converting a sulphide or a sulphoxide to a sulphone, at least two or at least one, respectively, molar equivalent(s) of oxidising agent are required for an efficient conversion.

2) All the compounds of the formula (I) may be prepared by reacting an organometallic compound of the formula:

  (II)

wherein M is a suitable metal, e.g. lithium, sodium or potassium, or metal halide derivative, e.g. a magnesium halide derivative (i.e. a Grignard reagent), and $R^1$, $R^2$, $R^3$, $R^4$ and m are as previously defined for a compound of the formula (I), with a compound of the formula:

  (IV)

wherein R is as previously defined for a compound of the formula (I).

The organometallic compounds of the formula (II) wherein M is a suitable metal are preferably generated in situ by deprotonation of the corresponding alkylheterocycle of the formula:

  (III)

wherein $R^1$, $R^2$, $R^3$, $R^4$ and m are as previously defined for this method, with a suitable base, e.g. lithium diisopropylamide or lithium, sodium or potassium bis(trimethylsilyl)amide.

The organometallic compounds of the formula (II) wherein M is a suitable metal halide derivative, e.g. a magnesium halide derivative, can be prepared by treatment of the corresponding organometallic compound of the formula (II) wherein M is lithium in situ with a suitable metal halide, e.g. magnesium bromide.

The reaction is typically carried out under an inert atmosphere of nitrogen or argon and in a suitable organic solvent, e.g. tetrahydrofuran, at from –80° C. to –40° C., preferably at from –75° C. to –65° C., when M is a suitable metal, and at from –80° C. to the reflux temperature of the solvent when M is a suitable metal halide derivative.

The alkylheterocycles of the formula (III) may be prepared by conventional methods.

The compounds of the formula (IV) are either known, e.g. see EP-A-044605, EP-A-069442 or GB-A-1464224, or may be prepared by a similar methods thereto.

All the compounds of the formula (I) may be prepared by reacting a compound of the formula:

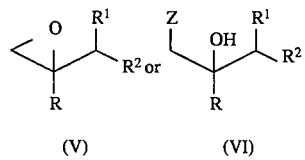

(V)        (VI)

wherein Z is a leaving group and R, $R^1$ to $R^4$ and m are as previously defined for a compound of the formula (I), either with 1H-1,2,4-triazole in the presence of a base or with a base salt of triazole.

Examples of Z are halo, e.g. chloro and bromo, and $C_1$–$C_4$ alkanesulphonyloxy methanesulphonyloxy).

Examples of suitable bases are sodium and potassium carbonate and hydroxide.

Examples of suitable base salts of 1H-1,2,4-triazole are the alkali metal, preferably sodium and potassium, and tetraalkylammonium, preferably tetra-n-butylammonium, salts.

The reaction is preferably carried out using an oxirane of the formula (V) as the starting material. If a compound of the formula (VI) is used in this process it is probable that the reaction mechanism dictates, at least in part, that the corresponding oxirane of the formula (V) is formed in situ under the reaction conditions. In this respect the process is therefore similar to that using an oxirane of the formula (V) as the starting material.

The reaction is typically carried out in a suitable solvent, e.g. N,N-dimethylformamide, methanol or aqueous acetone, and at an elevated temperature, e.g. at above 50° C. or at the reflux temperature of the solvent.

The intermediates of the formulae (V) and (VI) may be prepared by conventional methods, e.g. see EP-A-0357241 or EP-A-0440372.

4) The compounds of the formula (I) wherein m is 0 and R and $R^1$ to $R^4$ are as previously defined for a compound of the formula (I) may be prepared by reaction of a compound of the formula:

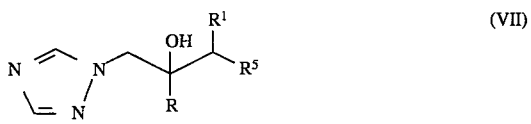  (VII)

wherein $R^5$ is

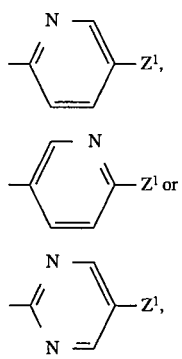

$Z^1$ is a leaving group, e.g. halo, preferably chloro, and R and $R^1$ are as previously defined for this method, with a base salt of a $C_1$–$C_4$ alkanethiol, e.g. an alkali metal salt, preferably the sodium salt.

The reaction is typically carried out in a suitable solvent, e.g. N,N-dimethylformamide, at about room temperature.

The intermediates of the formula (VII) may be prepared by conventional methods such as by a similar procedure to that described in method (2), (3) or (5) herein.

5) The compounds of the formula (I) wherein $R^1$ is $C_1$–$C_4$ alkyl with the exception of tert-butyl and R, $R^2$ to $R^4$ and m are as previously defined for a compound of the formula (I) may be prepared by reduction of a compound of the formula:

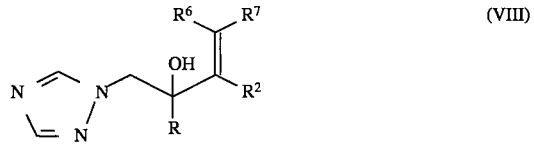  (VIII)

wherein $R^6$ and $R^7$ are each independently selected from H and $C_1$–$C_3$ alkyl with the proviso that if $R^6$ and $R^7$ are both $C_1$–$C_3$ alkyl then the total number of carbon atoms in both alkyl groups is not more than three, and R, $R^2$ to $R^4$ and m are as previously defined for this method.

The reduction is conveniently carried out using para-toluenesulphonhydrazide in a suitable organic solvent, e.g. toluene, at an elevated temperature, e.g. at the reflux temperature of the solvent.

The reduction may also be carried out by catalytic hydrogenation using a suitable catalyst, e.g. palladium/charcoal, and in a suitable solvent, e.g. a $C_1$–$C_4$ alkanol.

Certain intermediates of the formula (VIII) are disclosed in general terms by WO89/05581 and are prepared by the methods described therein. The remaining intermediates of the formula (VIII) may be prepared using similar procedures.

6) The compounds of the formula (I) wherein m is 0 and R and $R^1$ to $R^4$ are as previously defined for a compound of the formula (I) may be prepared by reduction of a compound of the formula (I) wherein m is 1 and R and $R^1$ to $R^4$ are as previously defined for this method.

The reduction may be carried out using a conventional method, e.g. see March, J., "Advanced Organic Chemistry", Third Edition, (John Wiley and Sons), such as by using titanium (III) chloride.

The compounds of the formula (I) wherein $R^2$ is

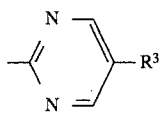

and R, $R^1$, $R^3$, $R^4$ and m are as previously defined for a compound of the formula (I) may be prepared by reduction of a compound of the formula:

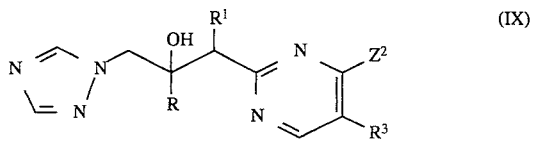

wherein $Z^2$ is a group that can be replaced by hydrogen by reduction, e.g. halo, preferably chloro, and R, $R^1$, $R^3$, $R^4$ and m are as previously defined for this method.

If $Z^2$ is halo, preferably chloro, a convenient method of reduction is by hydrogenolysis using a suitable catalyst, e.g. palladium/charcoal, and a suitable solvent, e.g. a $C_1$–$C_4$ alkanol, optionally in the presence of a suitable base, e.g. sodium acetate. The hydrogenolysis may be carried out at an elevated temperature and/or pressure if required.

The intermediates of the formula (IX) may be prepared by a similar procedure to that described in method (2) or (3) for the preparation of compounds of the formula (I) herein. The necessary starting materials of the formula:

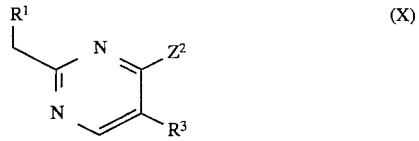

wherein $R^1$, $R^3$, $R^4$, m and $Z^2$ are as previously defined for this method, for use in this procedure or for use in the preparation of intermediates for use in this procedure may be prepared by a conventional method such as from a pyrimidinone described in Ger. Offen. 2,639,256 (see Chem. Abs., 89, 43764g).

All of the above reactions are conventional and appropriate reagents and reaction conditions for their performance and procedures for isolating the desired products will be well known to those skilled in the art, in accordance with literature precedents and by reference to the Examples and Preparations hereto.

A pharmaceutically acceptable acid addition salt is readily prepared by mixing together solutions containing the free base and the desired acid. The salt generally precipitates from solution and is collected by filtration, or is recovered by evaporation of the solvent.

The compounds of the formula (I) and their salts are antifungal agents, useful in the curative or prophylactic treatment of fungal infections in animals, including humans. For example, they are useful in treating topical fungal infections in man caused by, among other organisms, species of Candida, Trichophyton, Microsporum or Epidermophyton, or in mucosal infections caused by *Candida albicans* (e.g. thrush and vaginal candidiasis). They can also be used in the treatment of systemic fungal infections caused by, for example, species of Candida (e.g. *Candida albicans*), *Cryptococcus neoformans, Aspergillus flavus, Aspergillus fumigatus,* Coccidioides, Paracoccidioides, Histoplasma or Blastomyces.

The compounds of the formula (I) have been found to have unexpectedly good activity against the clinically important *Cryptococcus spp.* fungi and also have surprisingly reduced liver toxicity.

The compounds of the formula (I) wherein m is 0 or 1 and R and $R^1$ to $R^4$ are as previously defined for a compound of the formula (I) not only have antifungal activity per se but probably are also oxidised in vivo to give the corresponding compounds of the formula (I) wherein m is 2 and R and $R^1$ to $R^4$ are as previously defined for a compound of the formula (I).

The in vitro evaluation of the antifungal activity of the compounds can be performed by determining the minimum inhibitory concentration (m.i.c.), which is the concentration of the test compounds, in a suitable medium, at which growth of the particular micro-organism fails to occur. In practice, a series of agar plates, or liquid medium in microtiter plates, each having the test compound incorporated at a particular concentration, is inoculated with a standard culture of, for example, *Cryptococcus neoformans,* and each plate is then incubated for 48 hours at 37° C.. The plates are then examined for the presence or absence of growth of the fungus and the appropriate m.i.c. value is noted. Other micro-organisms used in such tests can include *Candida albicans, Aspergillus fumigatus, Trichophyton spp., Microsporum spp., Epidermophyton floccosum, Coccidioides immitis* and *Torulopsis glabrata.*

The in vivo evaluation of the compounds can be carried out at a series of dose levels by intraperitoneal or intravenous injection, or by oral administration, to mice or rats which are inoculated with, e.g., a strain of *Candida albicans, Aspergillus fumigatus* or *Cryptococcus neoformans.* Activity may be based on the number of survivors from a treated group of mice after the death of an untreated group of mice.

For *Candida spp.* infection models the dose level at which the compound provides 50% protection against the lethal effect of the infection ($PD_{50}$) is also assessed.

For *Aspergillus spp.* infection models the number of mice cured of the infection after a set dose allows further assessment of activity.

For *Cryptococcus spp.* infection models the number of colony forming units existing after a set dose is assessed and compared with control to determine compound efficacy. A preliminary assessment of potential liver toxicity may also be made on the basis of increase in liver weight relative to control.

For human use, the antifungal compounds of the formula (I) and their salts can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs, solutions or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

The solubility of a compound of the formula (I) in an aqueous medium may be improved by complexation with a hydroxyalkyl derivative of a cyclodextrin in the preparation of an appropriate pharmaceutical composition. Preferably the cyclodextrin used is alpha-, beta-, or gamma-cyclodextrin.

For oral and parenteral administration to human patients, the daily dosage level of the antifungal compounds of the formula (I) and their salts will be from 0.01 to 20 mg/kg (in single or divided doses). Thus tablets or capsules of the compounds will contain from 5 mg to 0.5 g of active compound for administration singly or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

Thus the invention further provides a pharmaceutical composition comprising a compound of the formula (I), or a pharmaceutically acceptable salt thereof, together with a pharmaceutically acceptable diluent or carrier.

The invention yet further provides a compound of the formula (I), or a pharmaceutically acceptable salt or composition thereof, for use as a medicament.

The invention also provides the use of a compound of the formula (I), or of a pharmaceutically acceptable salt or composition thereof, for the manufacture of an antifungal agent.

The invention yet further provides a method of treating an animal, including a human being, to cure or prevent a fungal infection which comprises treating said animal with an effective amount of a compound of the formula (I) or with a pharmaceutically acceptable salt or composition thereof.

The invention also includes the intermediates of the formulae (V), (VI), (VII), (VIII) and (IX).

The following Examples illustrate the preparation of the compounds of the formula (I):

EXAMPLE 1

(2R,3S/2S,3R)-2-(2,4-Difluorophenyl)-3-(2-methanesulphonylpyridin-5-yl)-1-(1H-1,2,4-triazol-1-yl)-butan- 2-ol A solution of (2R,3S/2S,3R)-2-(2,4-difluorophenyl)-3-(2-methylthiopyridin-5-yl)-1-(1H-1,2,4-triazol-1-yl)-butan- 2-ol (see Example 3) (0.5 g, 1.3 mmol) in dichloromethane (10 ml) at −70° C. was treated with a solution of m-chloroperoxybenzoic acid (80% pure, 0.62 g, 2.8 mmol) in dichloromethane (20 ml). The mixture was warmed to room temperature over 1 hour and then was washed with aqueous sodium hydroxide (2N, 20 ml), dried ($MgSO_4$) and evaporated under reduced pressure. The crude product was triturated with ethyl acetate to give the title compound, (0.25 g), m.p. 111°–114° C. Found: C,52.89; H,4.38; N,13.46; $C_{18}H_{18}F_2N_4O_3S$ requires: C,52.94; H,4.44; N,13.72%.

EXAMPLE 2

(2R,3S/2S,3R)-2-(2,4-Difluorophenyl)-3-(2-methylsulphinylpyridin-5-yl)-1-(1H-1,2,4-triazol-1-yl)-butan- 2-ol A solution of (2R,3S/2S,3R)-2-(2,4-difluorophenyl)-3-(2-methylthiopyridin-5-yl)-1-(1H-1,2,4-triazol-1-yl)-butan- 2-ol (see Example 3) (0.9 g, 2.3 mmol) in dichloromethane (20 ml) at −70° C. was treated with a solution of m-chloroperoxybenzoic acid (450 mg) in dichloromethane (10 ml). The mixture was warmed to room temperature over 1 hour and was then washed with aqueous sodium hydroxide solution (2N, 20 ml), dried ($MgSO_4$) and evaporated under reduced pressure. The residue was purified by flash chromatography on silica by elution with dichloromethane/methanol (98:2). The fractions containing the desired product were combined, evaporated under reduced pressure and then recrystallised from ethyl acetate/methanol to afford the title compound, (0.17 g), m.p. 182°–186° C.. Found: C,54.74; H,4.59; N,13.99; $C_{18}H_{18}F_2N_4O_2S$ requires: C,55.09; H,4.62; N,14.28%.

EXAMPLE 3

(2R,3S/2S,3R)-2-(2,4-Difluorophenyl)-3-(2-methylthiopyridin-5-yl)-1-(1H-1,2,4-triazol-1-yl)-butan- 2-ol A suspension of 2-(2,4-difluorophenyl)-3-(2-methylthiopyridin- 5-yl)-1-(1H-1,2,4-triazol-1-yl)-3-buten- 2-ol (see Preparation 1) (3.5 g, 9.4 mmol) and p-toluenesulphonhydrazide (18.6 g, 100 mmol) in toluene (100 ml) was heated under reflux for 20 hours. The mixture was cooled then partitioned between ethyl acetate (100 ml) and aqueous sodium hydroxide solution (2N, 50 ml). The organic layer was dried ($MgSO_4$) and then evaporated under reduced pressure. The residue was purified by flash chromatography on silica by elution with ethyl acetate. The desired enantiomeric pair eluted first and the relevant fractions were combined and evaporated under reduced pressure. The crude product was triturated with ether to afford the title compound as a colourless solid, (0.49 g), m.p. 120°–122° C.. Found: C,57.78; H,4.78; N,15.14; $C_{18}H_{18}F_2N_4OS$ requires C,57.43; H,4.82; N,14.88%.

EXAMPLE 4

(2R,3R/2S,3S)- and (2R,3S/2S,3R)-2-(2,4-Difluorophenyl)-3-(5-methylthiopyridin-2-yl)-1-(1H-1,2,4-triazol-1-yl)butan-2-ol A solution of 2-ethyl-5-methylthiopyridine (see Preparation 2) (1.4 g, 9.1 mmol) in tetrahydrofuran (THF) (10 ml) was added to a solution of lithium diisopropylamide (formed from diisopropylamine [1.3 ml, 9.1 mmol] and n-butyllithium solution [2.5M in hexane, 3.7 ml] in THF [40 ml])

at −70° C. under an atmosphere of dry $N_2$. The solution was stirred for 45 minutes at −70° C. and was then treated dropwise with a solution of 1-(2,4-difluorophenyl)- 2-(1H-1,2,4-triazol-1-yl)ethanone (2.0 g, 9.1 mmol) in THF (25 ml). The solution was stirred for 30 minutes at −70° C. then warmed to 0° C. and quenched by addition of aqueous acetic acid (10%, 50 ml). The mixture was partitioned between ethyl acetate (100 ml) and water (100 ml) and the aqueous phase further extracted with ethyl acetate (100 ml). The combined extracts were dried ($MgSO_4$) then evaporated under reduced pressure. Flash chromatography of the residue on silica eluting with ethyl acetate/hexane (1:1) initially gave, after combination and evaporation of the appropriate fractions and trituration with ether/hexane, the title compound, (2R,3S/2S,3R)-enantiomeric pair, (0.36 g), m.p. 105°–106° C. Found: C,57.37; H,4.82; N,14.84; $C_{18}H_{18}F_2N_4OS$ requires: C,57.43; H,4.77; N,14.88%.

$^1$H-NMR (300 MHz, $CDCl_3$): δ=1.03(d,3H), 2.54(s,3H), 3.62(q,1H), 4.04(d,1H), 4.72(d,1H), 6.79(m,2H), 7.22(m, 2H), 7.52(q,1H), 7.59(s,1H), 7.61(dd,1H), 7.96(s,1H), 8.43(d,1H) ppm.

After further elution of the column and combination and evaporation of the appropriate fractions the title compound, (2R,3R/2S,3S)- enantiomeric pair, was obtained as a yellow gum, (0.38 g). Found: C,57.79; H,4.98; N,14.39; $C_{18}H_{18}F_2N_4OS$ requires: C,57.43; H,4.77; N,14.88%.

$^1$H-NMR (300 MHz, $CDCl_3$): δ=1.52(d,3H), 2.39(s,3H), 3.72(q,1H), 4.66(d,1H), 4.80(d,1H), 6.43(td,1H), 6.60(td, 1H), 6.82(d,1H), 7.02(q,1H), 7.03(broad s,1H ), 7.30(dd, 1H), 7.60(s,1H), 8.04(s,1H), 8.20(d,1H) ppm.

EXAMPLE 5

(2R,3S/2S,3R)-2-(2,4-Difluorophenyl)-3-(5-methanesulphonylpyridin-2-yl)-1-(1H-1,2,4-triazol-1-yl)-butan- 2-ol A solution of (2R,3S/2S,3R)-2-(2,4-difluorophenyl)-3-(5-methylthiopyridin-2-yl)-1-(1H-1,2,4-triazol-1-yl)-butan- 2-ol (see Example 4) (0.75 g, 2 mmol) in dichloromethane (30 ml) was treated with a solution of m-chloroperoxybenzoic acid (80% pure, 1.1 g, 5 mmol) in dichloromethane (10 ml) at −60° C. The reaction mixture was warmed to room temperature, stirred for 1 hour then washed with saturated sodium hydroxide solution (2M, 50 ml), and dried ($MgSO_4$). The organic layer was evaporated under reduced pressure. The residue was recrystallised from ethyl acetate to give the title compound as a white solid, (490 mg), m.p. 159°–161° C. Found: C,52.91; H,4.34; N,13.65; $C_{18}H_{18}F_2N_4O_3S$ requires: C,52.94; H,4.44; N,13.72%.

EXAMPLE 6

(2R,3S)- and (2S,3R)-2-(2,4-Difluorophenyl)-3-(5-methylthiopyridin-2-yl)-1-(1H-1,2,4-triazol-1-yl)butan- 2-ol The (2R,3S/2S,3R)- enantiomeric pair obtained according to Example 4 was resolved by H.P.L.C. using a chiral support (CHIRACEL AD) (trade mark) and eluting with hexane/isopropanol (85:15) at a flow rate of 1 ml/min. One enantiomer had a retention time=13.22 min. and the other enantiomer a retention time=15.97 min. The appropriate fractions were separately combined and evaporated to provide the resolved individual enantiomers, each contaminated with the chiral support.

Each impure enantiomer was then further purified by column chromatograpy on silica using dichloromethane/methanol (95:5) as the eluant. The appropriate fractions were combined and evaporated to give the purified, separated (2R,3S)- and (2S,3R)- enantiomers as colourless oils which were not characterised.

EXAMPLE 7

2-(2,4-Difluorophenyl)-3-(5-methanesulphonylpyridin-2-yl)-1-(1H-1,2,4-triazol-1-yl)butan-2-ol (believed to be the (2S,3R)-enantiomer The purified enantiomer with a H.P.L.C. retention time= 13.22 min. from Example 6 was oxidised by a similar procedure to that used in Example 5 to give the title compound, m.p. 176°–177° C., $[α]_D^{25}$ +44.1° (c=1 mg/ml in methanol). Found: C,52.52; H,4.35; N,13.42; $C_{18}H_{18}F_2N_4O_3S$ requires: C,52.94; H,4.44; N,13.72%.

EXAMPLE 8

2-(2,4-Difluorophenyl)-3-(5-methanesulphonylpyridin-2-yl)-1-(1H-1,2,4-triazol-1-yl)butan-2-ol (believed to be the (2R,3S)-enantiomer)

The purified enantiomer with a H.P.L.C. retention time= 15.97 min. from Example 6 was oxidised by a similar procedure to that used in Example 5 to give the title compound, m.p. 176°–177° C., $[α]_D^{25}$ −30.7° (c=1 mg/ml in methanol). Found: C,52.61; H,4.18; N,13.30; $C_{18}H_{18}F_2N_4O_3S$ requires: C,52.94; H,4.44; N,13.72%.

The following Preparations illustrate the preparation of certain starting materials used in the preceding Examples:

PREPARATION 1
2-(2,4-Difluorophenyl)-3-(2-methylthiopyridin-5-yl)-1-(1H-1,2,4-triazol-1-yl)-3-buten-2-ol

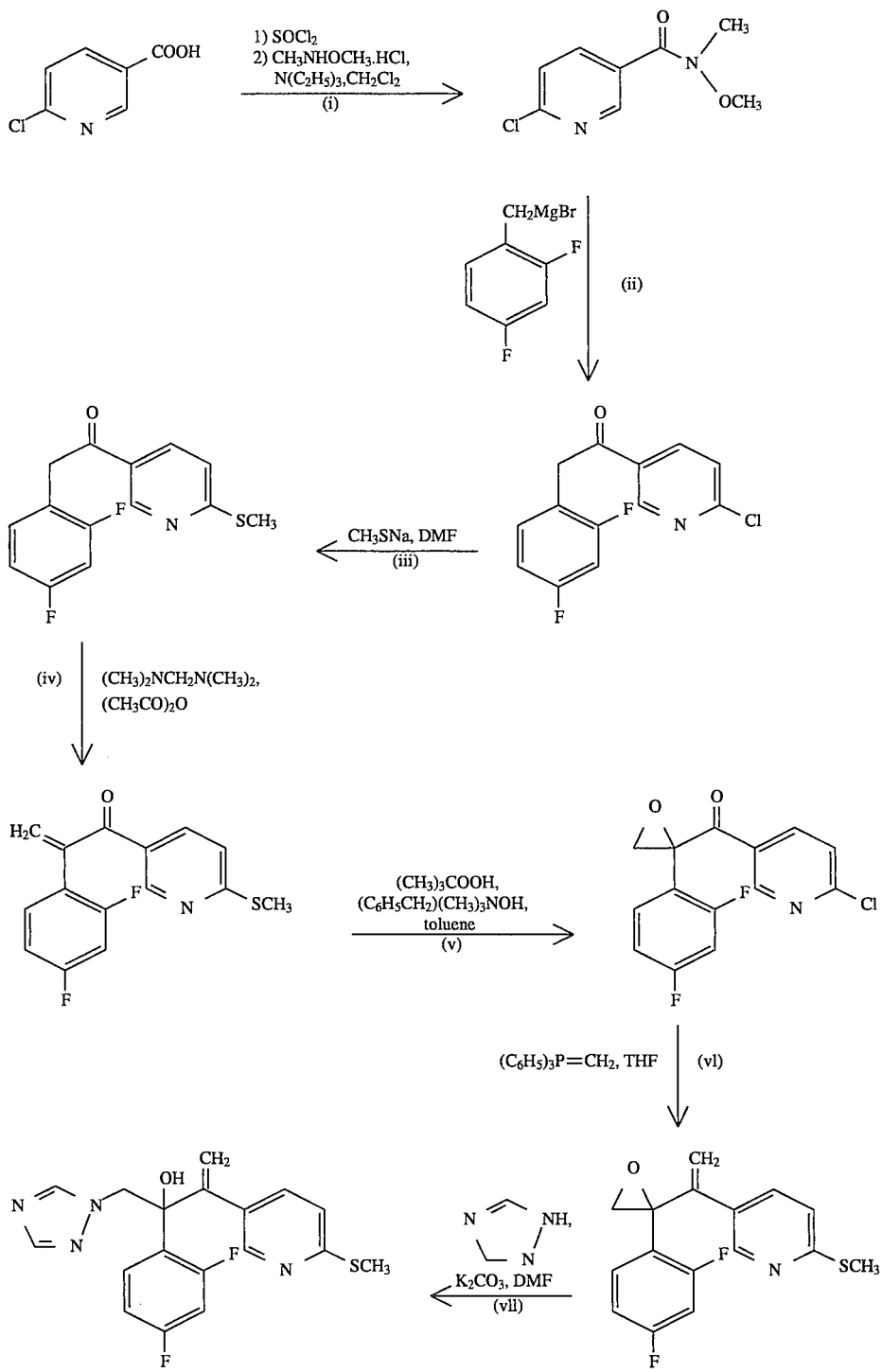

(i) N-Methoxy-N-Methyl-6-chloronicotinamide

A mixture of 6-chloronicotinic acid (80 g, 0.48 mmol) and thionyl chloride (400 ml) was heated under reflux for 3 hours. The cooled mixture was evaporated under reduced pressure and the residue was dissolved in dichloromethane (600 ml). N,O-dimethylhydroxylamine hydrochloride (54.6 g, 0.56 mmol) was added to the mixture which was then cooled in ice and treated with triethylamine (200 ml). The suspension was stirred for 1 hour at room temperature and was then filtered. The filtrate was washed with dilute sodium hydroxide solution (2N, 300 ml), brine (200 ml) and dried (MgSO$_4$). The solution was evaporated under reduced pressure then distilled to give the title compound, (90 g), b.p. 106°–110° C. at 0.5 mm.

¹H-NMR (300 MHz, CDCl₃): δ=3.38(s,3H), 3.56(s,3H), 7.39(d,1H), 8.02(dd,1H), 8.78(d,1H) ppm.

(ii) 1-(2-Chloropyridin-5-yl)-2-(2,4-difluorophenyl)ethanone 2,4-Difluorobenzyl bromide (9.0 ml, 70 mmol) was added dropwise to a suspension of magnesium (1.8 g, 75 mmol) in diethyl ether (50 ml) under an atmosphere of dry nitrogen at a sufficient rate to maintain a gentle reflux. The resulting solution was stirred for 15 minutes at room temperature and was then added dropwise to a solution of the product of part (i) (10.0 g, 50 mmol) in THF (70 ml) at −70° C. under an atmosphere of nitrogen. The mixture was warmed to room temperature, stirred for 2 hours then quenched with dilute hydrochloric acid (2M, 50 ml). The layers were separated and the aqueous phase was extracted with diethyl ether (2×50 ml). The combined extracts were dried (MgSO₄) and evaporated under reduced pressure. The residue was purified by flash chromatography on silica by elution with ether/hexane (1:1). The appropriate fractions were combined, evaporated under reduced pressure and the crude product was triturated with diethyl ether to give the title compound as a yellow solid, (10.7 g), m.p. 93°–95° C. Found: C,58.01; H,2.99; N,5.17; C₁₃H₈ClF₂NO requires: C,58.33; H,3.01; N,5.23%.

¹H-NMR (300 MHz, CDCl₃): δ=4.26(s,2H), 6.88(m,2H), 7.20(q,1H), 7.46(d,1H), 8.22(dd,1H), 9.00(d,1H) ppm.

(iii) 2-(2,4-Difluorophenyl)-1-(2-methylthiopyridin-5-yl)ethanone

A solution of the product of part (ii) (23.9 g, 89 mmol) in N,N-dimethylformamide (DMF) (105 ml) was treated with sodium methanethiolate (6.6 g, 94 mmol) and the resulting suspension was stirred for 2 hours at room temperature. The mixture was poured into diethyl ether (1000 ml) and the suspension was washed with water (2×500 ml). The organic phase was dried (MgSO₄) and evaporated under reduced pressure. The crude product was triturated with diethyl ether to afford the title compound as a yellow solid, (3.3 g).

¹H-NMR (300 MHz, CDCl₃): δ=2.65 (s,3H), 4.27(s,2H), 6.90(m,2H), 7.23(q, 1H), 7.29(d,1H), 8.08(dd,1H), 9.07(d, 1H) ppm.

(iv) 2-(2,4-Difluorophenyl)-1-(2-methylthiopyridin-5-yl)prop- 2-en-1-one

N,N,N',N'-Tetramethyldiaminomethane (5.2 ml, 38 mmol) was added to a stirred mixture of the product of part (iii) (7.2 g, 26 mmol) and acetic anhydride (3.6 ml, 38 mmol) and the reaction temperature was moderated by use of water bath at ambient temperature. After 1 hour at room temperature the yellow solution was poured onto ice and the mixture extracted with ethyl acetate (2×75 ml). The combined organic layers were washed with dilute hydrochloric acid (0.2M, 50 ml) followed by saturated sodium bicarbonate solution (50 ml), then dried (MgSO₄) and evaporated under reduced pressure. The residue was purified by flash chromatography on silica by elution with ether/hexane (1:4) to give the title compound as a yellow solid, (3.8 g).

¹H-NMR (300 MHz, CDCl₃): δ=2.64(s,3H), 5.95(s,1H), 6.16(s,1H), 6.86(m,1H), 6.97(m,1H), 7.29(d,1H), 7.41(q, 1H), 8.00(dd,1H), 8.90(d,1H) ppm.

(v) 2-(2,4-Difluorophenyl)-2-((2-methylthiopyridin-5-yl)carbonyl)oxirane

A solution of the product of part (iv) (3.8 g, 13 mmol) in toluene (40 ml) was treated with a solution of t-butylhydroperoxide in 2,2,4-trimethylpentane (3M, 4.7ml, 14 mmol) followed by a solution of benzyltrimethylammonium hydroxide in methanol (40%, 100 μl). After 1 hour at room temperature the solvent was removed under reduced pressure. The residue was partitioned between dichloromethane (100 ml) and water (50 ml). The organic phase was separated, dried (MgSO₄) and evaporated under reduced pressure to give the title compound as a colourless oil, (3.9 g).

¹H-NMR (300 MHz, CDCl₃): δ=2.58(s,3H), 3.22(d,1H), 3.40(d,1H), 6.80(m,1H), 6.92(m,1H), 7.21(d,1H), 7.47(q, 1H), 8.04(dd,1H), 9.03(d,1H) ppm.

(vi) 2-(2,4-Difluorophenyl)-2-(1-(2-methylthiopyridin-5-yl)ethenyl)oxirane

A suspension of methyltriphenylphosphonium bromide (5.0 g, 14 mmol) in THF (70 ml) was treated with n-butyllithium (2.5M solution in hexane, 5.6 ml, 14 mmol) under an atmosphere of nitrogen at −70° C. After 15 minutes at −70° C. the mixture was warmed to 0° C. and then was treated dropwise with a solution of the product of part (v) (3.9 g, 13 mmol) in THF (40 ml). The mixture was stirred at room temperature for 18 hours and then evaporated under reduced pressure. The residue was partitioned between dichloromethane (50 ml) and water (30 ml). The organic phase was dried (MgSO₄) and evaporated under reduced pressure. The crude product was purified by flash chromatography on silica by elution with ether/hexane (1:4) to provide the title compound as an orange oil, (3.6 g).

¹H-NMR (300 MHz, CDCl₃): δ=2.56(s,3H), 3.16(s,2H), 5.48(s,2H), 6.78(m,1H), 6.81(m,1H), 7.05(d,1H), 7.40(q, 1H), 7.58(dd,1H), 8.45(d,1H) ppm.

(vii) 2-(2,4-Difluorophenyl)-3-(2-methylthiopyridin-5-yl)- 1-(1H-1,2,4-triazol-1-yl)-3-buten-2-ol A solution of the product of part (vi) (3.6 g, 13 mmol) in DMF (30 ml) was added to potassium carbonate (2.0 g, 15 mmol) and 1H-1,2,4-triazole (1.0 g, 15 mmol). The mixture was stirred at 50° C. for 20 hours then poured into ethyl acetate (200 ml) and washed with water (2×100 ml). The organic phase was dried (MgSO₄) and evaporated under reduced pressure. Flash chromatography of the residue on silica by elution with ethyl acetate gave the title compound as an oil, (3.5 g).

¹H-NMR (300 MHz, CDCl₃): δ=2.58(s,3H), 4.61(d,1H), 4.98(d,1H), 5.30(s,1H), 5.32(broad s,1H), 5.35(s,1H), 6.75(m,2H), 7.08(d,1H), 7.42(m,1H), 7.50(dd,1H), 7.80(s, 1H), 7.84(s,1H), 8.37(d,1H) ppm.

PREPARATION 2

2-Ethyl-5-methylthiopyridine (i) 5-Bromo-2-ethylpyridine

A solution of ethylmagnesium chloride (2M in diethyl ether, 21.1 ml, 42.2 mmol) was added to dry THF (75 ml) and then treated with zinc chloride solution (1.0M in diethyl ether, 42.2 ml, 42.2 mmol). The suspension was stirred for 30 minutes at room temperature and was then cooled in ice. Tetrakis-(triphenylphosphine)palladium(0) (0.5 g) was added to the suspension followed by a solution of 2,5-dibromopyridine (5.0 g, 21.1 mmol) in THF (25 ml). The mixture was stirred at 5° C. for 5 hours and then shaken with a suspension of ethylenediamine-tetraacetic acid, disodium salt dihydrate (7.9 g, 21 mmol) in water (100 ml). The layers were separated and the aqueous phase was extracted with dichloromethane (50 ml). The combined organic layers were dried (MgSO₄) and evaporated under reduced pressure. The residue was distilled under reduced pressure (60 mm) at an oven temperature of 180° C. using a Kugelrohr (trade mark) apparatus to give the title compound, (2.25 g).

$^1$H-NMR (300 MHz, CDCl$_3$): δ=1.27(t,3H), 2.79(q,2H), 7.05(d,1H), 7.70(dd,1H), 8.58(d,1H) ppm.

(ii) 2-Ethyl-5-methylthiopyridine

A solution of 5-bromo-2-ethylpyridine (see part (i)) (3.0 g, 16.2 mmol) in dry DMF (4.5 ml) was treated with sodium methanethiolate (1.8 g, 24.3 mmol) and the suspension heated at 100° C. for 3 hours. The cooled mixture was diluted with diethyl ether (200 ml), washed with water (4×100 ml), then dried (MgSO$_4$) and evaporated under reduced pressure. The residue was purified by flash chromatography on silica by elution with dichloromethane. The appropriate fractions were combined and evaporated under reduced pressure. The resulting oil was distilled under reduced pressure (60 mm) at an oven temperature of 150° C. using a Kugelrohr (trade mark) apparatus to give the title compound, (1.4 g).

$^1$H-NMR (300 MHz, CDCl$_3$): δ=1.27(t,3H), 2.44(s,3H), 2.75(q,2H), 7.04(d,1H), 7.46(dd,1H), 8.40(d,1H) ppm.

COMPARATIVE PHARMACOLOGICAL DATA

The compound of Example 5 of the present Application was tested together with the compound of Example 2, diastereoisomeric pair B, of EP-A-0357241 and the compound of Example 2, enantiomeric pair B, of EP-A-0440372 for in vivo activity against *Cryptococcus neoformans* in rats using the following procedure, and the results are expressed in Table I.

A group of rats was inoculated intracranially with a strain of *Cryptococcus neoformans*. Each rat was then treated with a specified dose of the particular compound under test at 3 hours post-infection and then b.i.d. for 9 days. The rats were assessed on the tenth day by removal of brain tissue. The tissue was homogenised and the number of colony forming units per ml (C.F.U./ml) counted and compared with the number of C.F.U./ml found in the brain tissue of an untreated control group of rats. Results are expressed as the log. advantage relative to control.

TABLE I

| Compound of . . . | Dose (mg/kg) | Log. advantage |
|---|---|---|
| Example 5 of the present Application | 10 | 5.6 |
| | 5 | 5.17 |
| | 1 | 4.08 |
| | 0.1 | 2.13 |
| Example 2, diastereoisomeric pair B, of EP-A-0357241 | 25 | 3.99 |
| Example 2, enantiomeric pair B, of EP-A-0440372 | 20 | 4.01 |
| | 10 | 3.28 |
| | 5 | 3.37 |

We claim:

1. A compound of the formula:

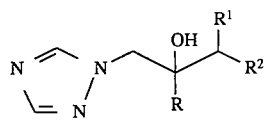

or a pharmaceutically acceptable salt thereof, wherein

R is phenyl substituted by up to 3 substituents each independently selected from halo and trifluoromethyl;

R$^1$ is C$_1$–C$_4$ alkyl;

R$^2$ is

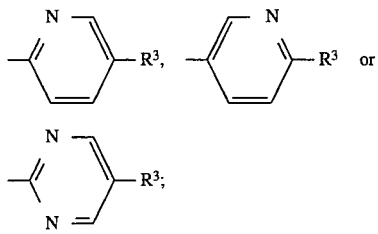

R$^3$ is —S(O)$_m$R$^4$;

R$^4$ is C$_1$–C$_4$ alkyl; and m is 0, 1 or 2.

2. A compound as claimed in claim 1 wherein R is phenyl substituted by 1 or 2 halo substituents.

3. A compound as claimed in claim 2 wherein R is phenyl substituted by 1 or 2 substituents each independently selected from fluoro and chloro.

4. A compound as claimed in claim 3 wherein R is 2,4-difluorophenyl.

5. A compound of claim 1 wherein R$^1$ is methyl.

6. A compound of claim 1 wherein R$^2$ is

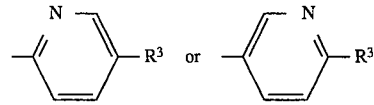

7. A compound of claim 1 wherein R$^4$ is methyl.

8. A compound of claim 1 wherein m is 2.

9. 2-(2,4-Difluorophenyl)-3-(2-methanesulphonylpyridin-5-yl)-1-(1H-1,2,4-triazol-1-yl)butan-2-ol or 2-(2,4-difluorophenyl)-3-(5-methanesulphonylpyridin-2-yl)-1-(1H-1,2,4-triazol-1-yl)butan-2-ol, or a pharmaceutically acceptable salt thereof.

10. A compound of claim 1 which has the (2R,3S)-stereochemical configuration, that is

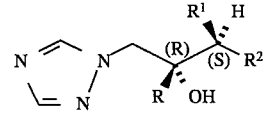

11. A pharmaceutical composition for the prevention or cure of a fungal infection comprising a compound of formula (I) as defined in claim 1, or a pharmaceutically acceptable salt thereof, in amount effective to prevent or cure said fungal infection together with a pharmaceutically acceptable diluent or carrier.

12. A method of treating an animal to cure or prevent a fungal infection which comprises administering to said animal an effective amount of a compound of the formula (I) or a pharmaceutically acceptable salt or composition thereof, as claimed in claim 1.

* * * * *